United States Patent [19]

Bombardelli et al.

[11] Patent Number: 5,431,923
[45] Date of Patent: *Jul. 11, 1995

[54] TOPICAL COSMETIC AND/OR PHARMACEUTICAL COMPOSITIONS

[75] Inventors: Enzio Bombardelli, Milan; Cesare Ponzone, Vidigulfo; Pier P. Puglisi, Pharma, all of Italy

[73] Assignee: Indena S.p.A., Italy

[*] Notice: The portion of the term of this patent subsequent to Dec. 7, 2010 has been disclaimed.

[21] Appl. No.: 152,203

[22] Filed: Nov. 12, 1993

Related U.S. Application Data

[63] Continuation-in-part of Ser. No. 856,287, Mar. 24, 1992, Pat. No. 5,268,175.

[30] Foreign Application Priority Data

Feb. 17, 1992 [GB] United Kingdom ............... 9203299

[51] Int. Cl.$^6$ ............................................. A61K 7/02
[52] U.S. Cl. .................................... 424/401; 424/63; 424/195.1; 514/2; 514/15; 514/21; 514/938; 514/944

[58] Field of Search .............. 424/499, 195.1, 401, 424/63; 514/2, 15, 21, 938, 944

[56] References Cited

U.S. PATENT DOCUMENTS

| | | | |
|---|---|---|---|
| 4,283,386 | 8/1981 | Van Scott | 424/70 |
| 4,725,670 | 2/1988 | Grill | 530/326 |
| 4,883,861 | 11/1989 | Grill | 530/326 |
| 5,116,749 | 5/1992 | Grill | 435/193 |
| 5,268,175 | 12/1993 | Bombardelli | 424/499 |

*Primary Examiner*—Thurman K. Page
*Assistant Examiner*—Sally Gardner
*Attorney, Agent or Firm*—Kirschstein et al.

[57] ABSTRACT

Topical cosmetic and pharmaceutical compositions are provided for the external protection of human or animal tissues from contact with heavy metals, said compositions comprising a metal sequestering component capable of binding metal ions and a physiologically inert carrier suitable for topical administration. The said metal sequestering component comprises one or more metal binding peptide having a high proportion of cysteine residues, for example a metallothionein.

6 Claims, No Drawings

TOPICAL COSMETIC AND/OR PHARMACEUTICAL COMPOSITIONS

CROSS-REFERENCE TO RELATED APPLICATION

This application is a continuation-in-part of application Ser. No. 07/856,287 now U.S. Pat. No. 5,268,175 filed on Mar. 24, 1992.

DESCRIPTION OF THE INVENTION

This invention relates to cosmetic and/or pharmaceutical compositions for use in protecting human or animal tissues, especially epithelial tissues, from the damaging effects of contact with heavy metals.

Many metal ions are required by organisms in trace amounts as essential nutrients. For example, many functions carried out by polypeptides, e.g., enzymatic, structural and immunological functions, require metallic cofactors. However other metallic ions, in particular ions of the heavy metals, can adversely affect these functions, especially if the ions are present in non-physiological quantities. Thus, overexposure to metals in the environment can lead to toxic effects.

Ecological studies conducted in the industrialized countries of the world have shown that the amounts of these metals present in the environment are increasing. This has led to an increase in levels of heavy metals in the tissues of organisms, including man, through ingestion of contaminated foodstuffs and exposure to metals in, for example, the atmosphere.

The effects of an accumulation of heavy metal ions can be extremely dangerous and their toxicity is thought to be due in part to disruption of the tertiary and quaternary structure of proteins, causing reduction in catalytic, (i.e., enzymatic) activity.

The thus disrupted proteins may be antigenic and cause an immune response. In this regard they may be recognized by the body as "foreign polypeptide biotic agents" which cause an auto-immune response (many common allergies are caused by heavy metals, in association with use of detergents or other environmental factors).

A further mechanism that has been shown to be responsible for the toxic effects of metals is the competitive substitution of natural physiological enzymic cofactors by heavy metals when at non-physiological concentrations.

Thus, the control of heavy metal pollutants in the atmosphere is essential if metal-related diseases are to be prevented. It is therefore expedient to seek products that efficiently and selectively block heavy metal ions, rendering them incapable of entering the body and thereby preventing them exerting their toxic effects. The extensive contamination of the environment by heavy metals and their ubiquitous presence in the ecosystem, mean that the skin and the accessible mucous membranes form the largest surface area available on which heavy metals accumulate and subsequently are absorbed into the body. It is also known that many of the cutaneous allergic manifestations that have until now been attributed to detergents or other causes have now been shown to involve heavy metals in their aetiopathogenesis.

Of special note are copper, cobalt, zinc, manganese, mercury and nickel which present significant health hazards in the mining industry, and lead, from exhaust fumes. It has been postulated that the accumulation of lead in developing children may exert a deleterious effect on memory and powers of concentration.

It is an object of the invention to provide a topical cosmetic and/or pharmaceutical composition for protecting the skin of a human or animal from exposure to heavy metals. U.S. Pat. Nos. 4,725,670 (Grill) and 4,883,861 (Grill) disclose the extraction from plant material of metallothioneins and their use in the form of pharmaceutical preparations for treating acute and chronic heavy metal poisoning, and metal deficiency phenomena. The Grill compositions are suitable for internal consumption and use only. The Grill patents make no mention that metallothioneins may be used as protective agents against the effects of heavy metal ion contact.

It has now been surprisingly found that certain polypeptides having a capacity to sequester heavy metals can be used to manufacture cosmetic and/or pharmaceutical compositions which enable the aforementioned problems to be overcome.

Thus according to the present invention there is provided a topical cosmetic and/or pharmaceutical composition for the external protection of human or animal tissues from the toxic effect of contact with heavy metals, said composition comprising a metal sequestering component capable of binding metal ions and a physiologically inert carrier suitable for topical administration, characterised in that said metal sequestering component comprises one or more metal binding peptide having a high proportion of cysteine residues.

It is preferred that said metal-binding peptide comprises ligands capable of forming metal-thiolate clusters with heavy metal ions.

Thus, it is preferred that the metal-binding peptide has between about 10 and 50% cysteine residues, more preferably between about 25 and 45%, based on the total number of residues.

Metal binding peptides having a high proportion of cysteine exist in nature. Examples of such naturally-occurring peptides include the metallothioneins. A subclass of metallothioneins is the so-called phytochelatins. However many authorities now use the term "metallothionein" to cover both.

In more detail, metallothioneins (MTs) are a group of proteins, first discovered in equine kidney in studies on cadmium accumulation by Margoshes and Vallee in 1957. The apoprotein (devoid of bound metal ions) may be capable of binding more than one type of metal. Since then, MTs have been found to bind cadmium, zinc, copper, mercury, silver, gold, lead and bismuth, amongst others.

MTs have been isolated from the tissues of animals, plants and microorganisms. They are non-globular proteins, located intracellularly mainly in the cytoplasm and have been isolated in mammals in the greatest abundance from parenchymatous tissues of liver, kidney and intestines.

The classification and nomenclature of MTs referred to herein is that recommended by "The Committee on the Nomenclature of Metallothionein" from the First International Meeting on Metallothioneins and other Low Molecular Weight Metal-Binding Proteins in Zurich, July 1978.

Three classes of MT are now recognised, as follows: Class I

Included in this class are all polypeptides related in primary structure to equine renal MT. This material is characterised by the following features:
 (i) Molecular weight 6000–7000;
 (ii) High metal content;
 (iii) Characteristic amino acid composition (high cysteine content, no aromatic amino acids);
 (iv) Unique distribution of cysteine residues in the amino acid sequence;
 (v) Spectroscopic features characteristic of metal-thiolate complexes and metal-thiolate clusters.

Class II

This class comprises forms displaying only slight or no evolutionary correspondence in terms of primary structure to mammalian forms. Examples are MTs from sea urchin and *N. crassa*. They share however the same ability to form metal-thiolate complexes and metal-thiolate clusters as Class I MTs.

Class III

This class comprises homologous, atypical oligo- —and polypeptides of the general structure (Glu-Cys)$_n$X, where n=2–8 and X is an amino acid such as glycine of β-alanine. They are often preferred to as phytochelatins and have been isolated from plant and fungal tissue.

These MTs may occur as oligomeric structures composed of two or more chains, differing in weight from 500 to 2000 daltons, linked via metal-thiolate bridges and/of via disulphide bonds.

Thus, it can be seen that the term metallothionein encompasses an extremely wide variety of proteins varying in structure and size, but shaping a common capacity to bind metal ions in complexes with cysteine side chains to form discrete metal-thiolate clusters. The amino acid sequences of typical Class I, II and III metallothioneins ape shown below in Table I:

TABLE I

| Amino acid sequences of a Class I, II and II metallothionein. | |
|---|---|
| Organism | Amino Acid Sequence |
| Human (Class I) MT-2 | Ac-MDPNCSAA GDSCTCAGS CKCKE CKCTSCKKS CCSCCPVGCA KCAQGCICKGASDK CSCCA |
| *Saccharomyces cerevisiae* (Class II) | QNEGHECQC QCGSCKNNEQ CQKSCSCPTG CNSDDKCPCG NKS EETKKSCCSGK |
| *Rauvolfia serpentia* | (Glu—Cys)$_n$ Gly, n = 4–8 |

Polypeptides having the functional characteristics of metallothioneins as described above may be used in accordance with the invention. These may be characterised by having specific sequences within the peptide chain such as Cys-Cys, Cys-X-Cys, and Cys-X-Y-Cys wherein X and Y are residues other than Cys.

Thus the metal-binding peptide used in accordance with the invention may be a metallothionein of Class I, and/or II, and/or III as defined in accordance with the International Convention on nomenclature, although other metal-binding peptides having a high proportion of cysteine residues may be used.

The compositions of the invention are all anhydrous, water-repellant oily preparations or water-repellant water-oil emulsions considered as barrier creams. The compositions of the invention are not dispersible in water and therefore if administered via an oral route would not have any activity.

Preferably, the composition according to the invention is substantially free of heavy metal ions, in order that the metal sequestering facility is not impaired. Thus, preferably the metallothionein(s) present is/are apometallothionein(s).

It is preferred that the compositions of the invention are formulated in the form of gels, creams, ointments, or body lotions which are not suitable for oral consumption or use. Additionally, it is envisaged that the compositions of the invention are formulated to be applied to exposed parts of the body in the form of a barrier cream or cosmetic make-up foundation which may preferably comprise a dermatologically inert colouring agent and-/or perfume.

It is most preferred that the compositions are formulated in the form of a film-forming, water-resistant mixture which may comprise for example oils, waxes, emulsions of an oil and emulsions of a wax silicone oils or other similar inert hydrophobic carrier materials. It is of course desirable that such materials do not interact with sulfhydryl groups of the metal-binding peptide. The compositions ape preferably water resistant and preferably are capable of remaining on the skin throughout the normal activities of the day, whilst being capable of being removed simply by washing with a detergent such as soap.

The compositions of the invention preferably contain between about 0.01 and percent by weight of said metal-binding peptide, and most preferably between about 0.1 and 5 percent by weight of said metal-binding peptide.

Examples of excipients for compositions of the invention are excipients selected from:
 Cyclomethicone
 Stearal alkonium hectorite (Bentone 27, NL Chemical)
 Hydrogenated castor oil
 Hydroxyoctacosanyl hydroxystearate (Elfacos C$_{26}$, Atzo Chemical)
 Isostearylstearate
 Cetyl palmitate
 Peg 45, dodecylglycol copolymer (Elfacos TS9, Atzo Chemie)
 Isopropylmyristate
 Glyceryl mono-dipalmitostearate (Geleol, Gattefossé)
 Cetyl dimethicone copolyol (Abil EM 90, Th. Goldschmidt)
 Stearyl dimethicone (Abil Wax 9800)
 Caprylic/Capric triglycerides (Migliol 810, Dynamit-Nobel)
 Polyglyceryl-4-stearate (Witconiol 18F, Witco Organic)

As a rule, all these excipients are not used for formulations intended for oral use.

In a further embodiment of the present invention, there is provided a mask for the protection of human tissues from the hazardous effects of environmental, particularly airborne heavy metal ion contamination, said mask comprising a filter medium carrying an adsorbent material comprising a metal sequestering component capable of binding metal ions, characterised in that said metal sequestering agent comprises one or more metal-binding peptide having a high proportion of cysteine residues. Metal-binding peptides can, according to the invention, also be employed in disposable cartridges fop masks for the protection of human epithelial tissues from the hazardous effects of airborne heavy metal ion contact.

The metal-binding peptide used according to the invention may be capable of binding many of the heavy metal ions which may be present in the environment. However it is envisaged that it will be most important to protect against lead, cadmium, chromium, mercury, copper and nickel.

Metal-binding peptides useful in producing the compositions, methods, masks and disposable cartridges of the invention are of widespread occurrence and can be obtained from plants, and/or animals and/or microorganisms.

Although metal-binding peptides may be obtained from any of these sources for use in the invention, those obtained from plants or microorganisms are preferred.

For example EP-A 0,242,799 discloses a method for extracting metallothioneins from plant material and metallothioneins produced according to this method may advantageously be used in producing compositions according to the invention.

It will be appreciated that the use of a product of vegetable or microbial origin belonging to the metallothionein group therefore provides an effective "molecular" method of intercepting heavy metals. Using the method of the invention it is possible to bind the metals with a thiolic bond to a polypeptide structure and the bound metals are then prevented from diffusing into the body. This prevents the metals from exerting their toxic effects (e.g. enzymatic inhibition and immunological reactions).

The plants most suitable for use in producing metallothioneins are those, for example, belonging to the Cruciferae and Caryophyllaceae families.

Metallothionein can have the ability specifically to sequester selected metals and it is especially preferred, in accordance with the invention, to utilise metallothioneins which are adapted to sequester toxic metals, in preference to metals which serve a useful purpose in metabolism, such as copper or iron.

Thus it is especially preferred to use a metallothionein which has a relatively high capability to sequester chromium, nickel, lead and/or cadmium, but a relatively low ability to sequester copper or iron. It is possible to prepare metallothioneins that are adapted to sequester predetermined cation species by cultivating plants such as *Eruca sativa*, *Brassica napus*, etc. under glass or in open fields in areas of low contamination by the metals. Growth may then continue in the presence of appropriate salts of the selected heavy metal acting as inducer. Once the metallothioneins formed in response to the applied metal have been isolated, they may be treated to remove the heavy metal, thereby freeing the active centres to resequester the same metal when they come into contact with it again.

When incorporated in appropriate pharmaceutical or cosmetic products, these metallothioneins will block the specific metal, for example one involved in the aetiopathogenesis of a specific metal-associated toxic manifestation.

The extraction of metallothioneins from vegetable material is described in EP-A-0 242 799 and U.S. Pat. No. 5,116,749 and these metallothioneins can be used according to the invention. Useful metallothioneins can be obtained from vegetable matter, yeasts or microorganisms that contain them by means of extraction of vegetable or microbial material homogenates with water.

The homogenates may then be centrifuged to separate the cell residues, and the supernatant, after partial dilution with $C_{1-3}$ aliphatic alcohols or with $C_{3-6}$ aliphatic ketones, may be filtered to eliminate undesired glycoprotein products of high molecular weight and then concentrated to a reduced volume.

The crude metallothioneins (often still containing bound metal) portion may be separated from the aqueous extract after being rendered insoluble by adding $C_{1-3}$ aliphatic alcohols or $C_{3-6}$ aliphatic ketones. The precipitate can be resolubilized in water and re-precipitated in the same solvents at a predetermined ratio to water of between 40 and 90% so as to enable products with a low molecular weight such as simple sugars, amino acids and inorganic salts to be eliminated completely. The metallothioneins, whose molecular weight can vary between 500 and 8,000 depending on their origin, can then be purified from the precipitate by conventional methods known in the literature For example using Sephadex G-50 columns or by means of ultrafiltration with a suitable cut-off membrane.

After being isolated, the metallothioneins prior to their intended cosmetic or therapeutic use, may be treated with acid resins in an atmosphere of inert gases and in the presence of antioxidants to remove the cation.

In this form they may then be incorporated into preparations for application to the skin in formulations such as aqueous gels, cleansing milks, or simple emulsions. It will be understood that it is preferred that only excipients and surfactants that do not interfere with the sulfhydryl groups of the polypeptide may be used.

As an example of cosmetic treatment in accordance with the invention, the formulations can be applied to the exposed parts of the body such as the face, neck, legs, etc. This is preferably carried out in the mornings when one is going into areas with a high urban traffic density or staying in areas of high pollution.

At the end of the day, normal washing will remove from the skin the residue of the formulation that has retained the heavy metals over the course of the day, preventing them from being absorbed through the skin.

Suitable formulations can be applied to the hands or other parts of the body after prolonged use of detergents in order to cleanse the lipid layer and at the same time pick up any traces of contaminating metals.

The following examples illustrate suitable formulations for the compositions of the invention:

EXAMPLE I

Formulation of a gel containing Pb, Cr, Cd and Ni sequestering metallothioneins.

The formulation has the following percentage composition:

|  | % |
| --- | --- |
| Metallothioneins | 1 |
| Beeswax | 10 |
| Cyclosilicone pentamer | 53 |
| Vaseline | 30 |
| Stearal alkonium hectorite | 2 |
| Hydrogenated castor oil | 2 |
| Pyrogenic silica | 1 |
| Perfume | 1 |

EXAMPLE II body milk A/O

The formulation has the following percentage composition:

|  | % |
|---|---|
| Metallothioneins | 1 |
| Cetyl dimethicone copolyol | 5 |
| Tetraglyceryl stearate hexyl laurate | 3 |
| Stearyl dimethicone | 6 |
| Isopropyl myristate | 6 |
| Mineral oil | 4 |
| Triglycerides C8-10 | 3 |
| Glycerine | 5 |
| Vaseline | 3 |
| NaCl | 2 |
| Perfume | 0.5 |
| Water | 61.5 |

EXAMPLE III

|  | % |
|---|---|
| Metallothioneins | 1 |
| Cetyl palmitate | 10 |
| Cyclomethicone | 53 |
| Isostearylstearate | 30 |
| Stearal alkonium hectorite | 2 |
| Hydrogenated castor oil | 2 |
| Pyrogenic silica | 1 |
| Perfume | 1 |

EXAMPLE IV

|  | % |
|---|---|
| Metallothioneins | 0.5 |
| Hydroxyoctacosanyl hydroxystearate | 10 |
| Peg 45, dodecylglycol copolimer | 10 |
| Cyclomethicone | 30 |
| Isopropylmyristate | 40 |
| Glyceryl mono-,dipalmitostearate | 7 |
| Perfume | 0.5 |
| Colloidal silicon dioxide | 2 |

EXAMPLE V

|  | % |
|---|---|
| Metallothioneins | 1 |
| Cetyl dimethicone copolyol | 5 |
| Polyglyceryl-4-stearate | 3 |
| Stearyl dimethicone | 6 |
| Isopropyl myristate | 6 |
| Mineral oil | 4 |
| Caprilic/Capric triglycerides | 3 |
| Glycerine | 5 |
| Isostearylstearate | 3 |
| Sodium chloride | 2 |
| Perfume | 0.5 |
| Water | 61.5 |

EXAMPLE VI

Materials and Methods: Ten healthy female volunteers of ages ranging between 23 and 31 (average 25±3.7) were selected for the investigation. In the initial conditions an examination was made of the microcirculation of the skin of the cheeks, the biomicroscopoic observation being repeated 30 days after daily application (cf. annexed Report). A placebo (product A) was applied to the left cheek, a metallothionein-containing composition according to the invention (product B) being applied to the right cheek.

The products applied had the following percentual composition and were prepared at the Indena Laboratories:

| Placebo (Product A) | g |
|---|---|
| Polytrimethylsiloxysilicate/dimethicone | 3 |
| Mineral oil | 0.5 |
| Isopropyl lanolate | 3 |
| Stearic acid | 1 |
| Cetyl alcohol | 1 |
| Tea extract | 1.2 |
| Perfume | 0.2 |
| Water | 90.1 |
| Total | 100 |

| Genuine (Product B) | g |
|---|---|
| Metallothioneins (Pb - Cd specific) | 0.5 |
| Polytrimethylsiloxysilicate/dimethicone | 3 |
| Mineral oil | 0.5 |
| Isopropyl lanolate | 3 |
| Stearic acid | 1 |
| Tea extract | 1.2 |
| Perfume | 0.2 |
| Water | 89.6 |
| Total | 100 |

A quantity of approximately 1.5 g of these two formulations was separately applied, with a gentle massage, to half the face of the experimental subjects; application was performed in the morning. The treatment period selected was the winter period, since at that time there is very heavy pollution in city centres. The determinations of the heavy metals were carried out on the second day from the start of the experiment, using the following procedure.

The treated part was washed with a cotton wad impregnated with a 0.5% aqueous solution of citric acid, using approximately 5ml of solution to wash half the face. The acid solution was concentrated to 1 ml, the heavy metals being determined from said solution by atomic absorption.

Instrument: Automatic sequential spectrometer ARL 3410 ICP (inductively coupled plasma).

Procedure: Reference solutions of the selected metals were prepared containing between 0.01 and 0.05 ppm, whereafter said solutions were aspirated to obtain the lead and cadmium calibration lines at the wavelengths specific to the two elements, i.e.:

Pb=220,353 nm
Cd=226,502 nm.

Then the solution of the sample being examined was analyzed: the instrument automatically supplied the concentration of the two elements in ppm. No treatment of the sample was requested.

Limits of detectability: lead 0.0025 ppm cadmium 0.003 ppm.

Results:

The following Table shows the results of the investigation of the volunteers:

| Lead content (ppm) in the washing liquids of the skin of the half face treated with placebo (A) or genuine (B) | | |
|---|---|---|
| Case No. | Placebo | Genuine |
| 1 | 31.7 | 74.8 |
| 2 | 34.1 | 90.6 |
| 3 | 28.7 | 82.9 |
| 4 | 31.6 | 53.2 |

-continued

Lead content (ppm) in the washing liquids of the skin of the half face treated with placebo (A) or genuine (B)

| Case No. | Placebo | Genuine |
|---|---|---|
| 5 | 22.9 | 65.6 |
| 6 | 32.4 | 32.8 |
| 7 | 27.9 | 62.3 |
| 8 | 21.4 | 75.6 |
| 9 | 37.6 | 83.4 |
| 10 | 26.4 | 55.9 |
| Mean | 29.47 | 67.1 |

Cadmium content (ppm) in the washing liquids of the skin of the half face treated with placebo (A) or genuine (B)

| Case No. | Placebo | Genuine |
|---|---|---|
| 1 | 11.7 | 44.8 |
| 2 | 14.1 | 50.6 |
| 3 | 18.7 | 22.9 |
| 4 | 11.6 | 33.2 |
| 5 | 22.9 | 25.6 |
| 6 | 12.4 | 32.8 |
| 7 | 17.9 | 42.3 |
| 8 | 11.4 | 25.6 |
| 9 | 17.6 | 33.4 |
| 10 | 16.4 | 25.9 |
| Mean | 15.47 | 33.62 |

The contents of the two metals were higher in the solution obtained from the cheek treated with the product containing metallothionein, in comparison with the placebo, since the metallothionein retained the metal on the surface and inhibited its absorption.

EXAMPLE VII

We set up an experiment with the purpose of documenting the protective activities of the compositions of the invention on the skin microcirulation of women exposed to city traffic during the winter period.

MATERIALS AND METHODS

For the investigation 10 healthy female subjects were selected whose ages ranged between 23 and 31 (average age 25±3.7).

In the starting conditions an examination was made of the microcirculation in the skin of the cheeks, the biomicroscopic observation being repeated thirty days following daily application. A placebo (product A) was applied to the left cheek, a metallothionein-containing composition of the invention (product B) being applied to the right cheek. The instrument used was a hand-held video microscope imaging system (Scope Moritex MS509, Heisi, Japan), Formed by a telecamera, a computer, an optical probe and a monitor. Contact objectives D800× and D400× were selected. Prior to examination the skin was washed with luke warm water and dried with a cotton pad, whereafter a drop of microscopic immersion oil was deposited over an area and spread delicately over an area of approximately 2×2 cm. The object of this procedure was to make the horny layer more transparent.

OBSERVATIONS

The following Table shows the data obtained.

Capillary density of the skin of the cheeks in the initial conditions and after the administrations of products A and B for 30 days

| Case No. | Before (%) | After (%) A | After (%) B |
|---|---|---|---|
| 1 | 30.7 | 29.6 | 34.8 |
| 2 | 24.2 | 25.4 | 30.6 |
| 3 | 28.6 | 30.2 | 32.9 |
| 4 | 32.8 | 31.6 | 33.2 |
| 5 | 19.3 | 21.2 | 25.6 |
| 6 | 32.0 | 28.6 | 32.8 |
| 7 | 28.9 | 28.4 | 32.3 |
| 8 | 17.4 | 20.2 | 25.6 |
| 9 | 33.6 | 31.6 | 33.4 |
| 10 | 16.4 | 20.2 | 25.9 |
| Mean | 26 ± 2.0 | 26.7 ± 1.4 | 30.71 ± 1.1 |

From an examination of the Table it can be deduced that no statistically significant differences in comparison with the initial conditions were found in the cheeks treated with the placebo (A) after 30 days of application. In contrast, a statistically significant difference ($p<0.001$) was found in the cheeks treated with the composition of the invention (B).

CONCLUSIONS

The results clearly indicate that the protection by compositions of the invention of skin areas exposed to atmospheric pollution contaminated with heavy metals allows a statistically significant improvement in the blood irrigation, expressed in the increase in capillary density.

We claim:

1. A topical make-up foundation composition selected from the group consisting of water resistant gels, ointments and body lotions, said composition being for the external protection of human or animal tissues from contact with heavy metals and comprising (a) between about 0.01 and 10 percent by weight of said composition of a metallothionein and (b) a physiologically inert carrier which includes a water resistant, film forming substance selected from the group consisting of waxes, oils, emulsions of a wax and emulsions of an oil.

2. A composition according to claim 1 substantially free of heavy metal ions.

3. A composition according to claim 2 in which said metallothionein is an apometallothionein.

4. A composition according to claim 1 wherein said metallothionein is obtained from plants.

5. A composition according to claim 1 further comprising a dermatologically inert colouring agent.

6. A composition according to claim 1 comprising between about 0.1 and 5 percent by weight of said metallothionein.

* * * * *